(12) United States Patent
Tran et al.

(10) Patent No.: US 10,945,665 B1
(45) Date of Patent: Mar. 16, 2021

(54) ORAL DATA COLLECTION DEVICE

(71) Applicant: HOOT Medical Analytics, Inc., New York, NY (US)

(72) Inventors: Travis Tran, New York, NY (US); Konstantine Trichas, Montclair, NJ (US)

(73) Assignee: HOOT MEDICAL ANALYTICS, INC., New York, NY (US)

( * ) Notice: Subject to any disclaimer, the term of this patent is extended or adjusted under 35 U.S.C. 154(b) by 0 days.

(21) Appl. No.: 17/022,630

(22) Filed: Sep. 16, 2020

Related U.S. Application Data

(60) Provisional application No. 62/900,885, filed on Sep. 16, 2019.

(51) Int. Cl.
| | | |
|---|---|---|
| A61B 5/00 | (2006.01) | |
| A61B 5/22 | (2006.01) | |
| A61B 5/08 | (2006.01) | |
| A61B 5/11 | (2006.01) | |

(52) U.S. Cl.
CPC ............ *A61B 5/682* (2013.01); *A61B 5/0022* (2013.01); *A61B 5/082* (2013.01); *A61B 5/0816* (2013.01); *A61B 5/1114* (2013.01); *A61B 5/228* (2013.01); *A61B 5/4812* (2013.01); *A61B 5/4842* (2013.01); *A61B 5/4848* (2013.01); *A61B 5/4875* (2013.01); *A61B 5/7275* (2013.01); *A61B 2560/0214* (2013.01); *A61B 2562/0204* (2013.01); *A61B 2562/029* (2013.01); *A61B 2562/0219* (2013.01); *A61B 2562/0223* (2013.01); *A61B 2562/0247* (2013.01); *A61B 2562/0271* (2013.01); *A61B 2562/06* (2013.01)

(58) Field of Classification Search
None
See application file for complete search history.

(56) References Cited

U.S. PATENT DOCUMENTS

| | | |
|---|---|---|
| 5,078,153 A | 1/1992 | Nordlander et al. |
| 8,961,437 B2 | 2/2015 | Al-Tawil |
| 9,005,120 B2 | 4/2015 | Ryan |
| 9,791,336 B2 | 10/2017 | Zhu et al. |
| 9,814,391 B2 | 11/2017 | Hennig et al. |
| 10,117,010 B2 | 10/2018 | Spector et al. |
| 10,314,537 B2 | 6/2019 | Zegarelli |
| 2002/0094509 A1 | 7/2002 | Durbin et al. |
| 2005/0113654 A1 | 5/2005 | Weber et al. |

(Continued)

FOREIGN PATENT DOCUMENTS

WO  2008061328 A1  5/2008

OTHER PUBLICATIONS

International Search Report of International Application No. PCT/US2020/051014, dated Dec. 8, 2020.

*Primary Examiner* — Lynsey C Eiseman
*Assistant Examiner* — Amanda L Steinberg
(74) *Attorney, Agent, or Firm* — Polsinelli PC

(57) ABSTRACT

The present disclosure provides an oral data collection device comprising a mouthguard and at least two sensors, a medical analytics system comprising the device, and methods of using the device and system to provide a personalized treatment protocol, stage a health condition, measure a response to therapy, phenotype for selection to participate in drug trials, measure stability of an anatomical structure, or predict a rate of change of a health condition in a subject in need thereof.

18 Claims, 7 Drawing Sheets

(56) References Cited

U.S. PATENT DOCUMENTS

| | | |
|---|---|---|
| 2010/0036286 A1 | 2/2010 | Scholz et al. |
| 2010/0204747 A1 | 8/2010 | Lindquist |
| 2014/0288390 A1* | 9/2014 | Hong .................. A61B 5/02416 |
| | | 600/301 |
| 2014/0312834 A1 | 10/2014 | Tanabe et al. |
| 2014/0350354 A1 | 11/2014 | Stenzler et al. |
| 2015/0305671 A1* | 10/2015 | Yoon ..................... A61B 5/681 |
| | | 600/301 |
| 2016/0007849 A1* | 1/2016 | Krueger ............... A61B 5/1128 |
| | | 600/301 |
| 2016/0015321 A1 | 1/2016 | Hashemian |
| 2016/0095740 A1* | 4/2016 | Mardirossian .......... A61F 5/566 |
| | | 128/847 |
| 2016/0199216 A1* | 7/2016 | Cam ..................... A61C 7/002 |
| | | 128/848 |
| 2016/0242692 A1 | 8/2016 | McAuliffe et al. |
| 2017/0290699 A1* | 10/2017 | Radmand ............. A61B 5/4557 |
| 2018/0000563 A1* | 1/2018 | Shanjani ............. A61B 5/4818 |
| 2018/0035952 A1 | 2/2018 | Fraylick |
| 2018/0153469 A1 | 6/2018 | Yoon et al. |
| 2018/0196079 A1 | 7/2018 | Austin et al. |
| 2018/0242911 A1* | 8/2018 | Paris ........................ A61B 5/01 |
| 2018/0310881 A1 | 11/2018 | Yoon et al. |

\* cited by examiner

US 10,945,665 B1

ORAL DATA COLLECTION DEVICE

CROSS-REFERENCE TO RELATED APPLICATIONS

This application claims the benefit of U.S. Provisional Application No. 62/900,885, filed Sep. 16, 2019, the contents of which are incorporated herein by reference in their entirety.

FIELD OF THE INVENTION

The present disclosure provides an oral data collection device, a medical analytics system, and methods of using the device and system.

BACKGROUND OF THE INVENTION

Significant medical advancements in conjunction with higher computing power, lower hardware cost, and improved data management have led to an approach using a medical analytics approach to healthcare to be more holistically understood. In this era, there is a great deal of interest in wearable devices with functionality to collect up-to-date real-time health data.

Within the oral region of the human body, there are many other opportunities for the collection of invaluable health indicators. For instance, concern about injuries that occur during sporting activities has increased. In particular, head traumas that can result in concussion have come under greater scrutiny. According to the US Centers for Disease Control and Prevention (CDC), more than 3.8 million sports brain injuries occur per year with 300,000 resulting in loss of consciousness (LoC). These injuries are not limited to occurrence at the professional or collegiate level, but also include an estimated number of 25,000 sports brain injuries occurring at the high school level. Diagnosis and treatment of such injuries can be enhanced by monitoring athletes during the sporting events that can result in concussions and other head injuries. Importantly, oral health data can also be used to diagnose, monitor, and treat health conditions in a subject. For instance, oral data during sleep can provide invaluable information on a number of oral conditions and other health conditions that exhibit in data collected in the oral cavity, including bruxism, xerostomia, and PTSD. However, to date, there are no capabilities to continuously measure oral data during sleep. For instance, besides using the symptoms of bruxism that may be exhibited in the subject, including headaches, muscle soreness, daytime jaw discomfort/wear, and stress, methods of diagnosing or tracking the development of bruxism do not currently exist.

Accordingly, there is a need in the art for devices, systems, and methods of collecting oral data, especially oral data in the fitness and sports field, as well as when a subject is sleeping.

SUMMARY OF THE INVENTION

One aspect of the present disclosure encompasses an oral data collection device comprising a mouthguard and sensors. The mouthguard comprises an arch-shaped body comprising a proximal end, a first distal end, and a second distal end, an external surface, an internal surface, a first biting surface, and a tray operable to engage the upper or lower teeth of a subject, the tray comprising a second biting surface opposite the first biting surface. The device further comprises two or more sensors in the body of the mouthguard. The sensors comprise one or more pressure sensors, wherein each sensor is operable to sense biting force exerted by the upper and lower teeth of the subject at the first and second biting surfaces. The sensors also comprise a humidity sensor operable to sense relative humidity in the breath of a user wearing the device. A sensing surface of the humidity sensor can be at the internal surface off center of the proximal end of the mouthguard.

The device further comprises a controller in the body of the mouthguard, wherein the controller is in functional communication with the two or more sensors, and wherein the controller is operable to receive and communicate sensor data; a means for communication enclosed within the body of the mouthguard, wherein the means for communication is operable to receive the sensor data from the controller and communicate the sensor data to a secondary device; and a power source functionally coupled to the controller and the one or more sensors.

The device can comprise a first pressure sensor at the first distal end of the body of the mouthguard and a second pressure sensor at the second distal end of the body of the mouthguard. In some aspects, the pressure sensor is a pressure sensor stack. In some aspects, the device comprises a first pressure sensor stack at the first distal end of the mouthguard and a second pressure sensor stack at the second distal end of the mouthguard. The pressure sensor can be a force plate pressure sensor. Further, the pressure sensor can measure and withstand at least a pressure ranging from about 1 to about 5000 kPa, from about 100 to about 4000 kPa, or from about 100 to about 2000 kPa.

The device can further comprise a temperature sensor, a microphone or vibration sensor, an oxygen sensor, a nine-axis inertial sensor, a pH or other biochemical sensor, or combinations thereof. The nine-axis inertial sensor can be enclosed in the body of the mouthguard, and comprises a three-axis magnetometer, a three-axis accelerometer, and a three-axis gyroscope, the three-axis magnetometer operable to provide a reference plane in relation to earth's magnetic field for the three-axis accelerometer and the three-axis gyroscope, wherein the nine-axis inertial sensor is adapted to sense a position and movement of the head and body of a user.

When the device comprises a temperature sensor, humidity sensor, and oxygen sensor, the temperature sensor, humidity sensor, and oxygen sensor can be an integrated temperature, humidity, and oxygen sensor. The microphone or vibration sensor can be enclosed in an acoustic chamber in the body of the mouthguard.

The means of communication can comprise a transmitter operable to communicate sensor data to the secondary device wirelessly using a wireless communication protocol. The secondary device can be a desktop computer, a mobile computing device, a wearable device, a personal digital assistant, a computing device with no user interface, a cloud-computing platform, or a combination thereof. The power source can be a rechargeable battery.

In some aspects, the device further comprises a protective compartment housing one or more of the sensors, the controller, the means for communication, and the power source.

Another aspect of the present disclosure encompasses an oral data collection device. The device comprises a mouthguard comprising an arch-shaped body comprising a proximal end, a first distal end, and a second distal end, an external surface, an internal surface, a first biting surface, and a tray operable to engage the upper or lower teeth of a subject, the tray comprising a second biting surface opposite the first biting surface. The device further comprises sensors in the body of the mouthguard, the sensors comprising a first pressure sensor stack at the first distal end of the mouthguard and a second pressure sensor stack at the second distal end of the mouthguard, wherein each pressure sensor stack comprises a first pressure sensor and a second pressure sensor arranged in a stack; a humidity sensor operable to sense relative humidity in the breath of a user wearing the device; and a microphone or vibration sensor.

The device further comprises a controller in the body of the mouthguard, wherein the controller is in functional communication with the sensors, and wherein the controller is operable to receive and communicate sensor data; a means for communication in the body of the mouthguard, wherein the means for communication is operable to receive the sensor data from the controller and communicate the sensor data to a secondary device; and a power source functionally coupled to the controller and the one or more sensors.

Yet another aspect of the present disclosure encompasses medical analytics system comprising an oral data collection device and a secondary device comprising at least one processor and associated memory adapted to receive sensor data collected by the data collection device, and instructions which, when executed by the at least one processor, cause the at least one processor to interpret the sensor data obtained from a subject into descriptive factors indicative of a health condition of the subject; and output the descriptive factors. The descriptive factors indicative of a health condition of the subject can comprise hydration, breathing patterns, body temperature, body and head position, body and head movement, clenching of the jaws, sleep phase, and nighttime mouth position.

The secondary device can further comprise instructions which, when executed by the at least one processor, cause the at least one processor to provide a personalized treatment protocol, stage a health condition, measure a response to therapy, phenotype for selection to participate in drug trials, measure stability of an anatomical structure, or predict a rate of change of a health condition in the subject.

An additional aspect of the present disclosure encompasses a method of determining a personalized treatment protocol, staging a given health condition, measuring response to therapy, phenotyping for selection to participate in drug trials, measuring stability of an anatomical structure, or predicting rate of change of a health condition in a subject in need thereof. The method comprises providing or having provided the device described above to the subject for wearing by the subject during sleep, and interpret the sensor data obtained from the subject into descriptive factors indicative of a health condition of the subject to determine the personalized treatment protocol, stage the given health condition, measure response to therapy, phenotype for selection to participate in drug trials, measure stability of an anatomical structure, or predict rate of change of a given health condition in the subject.

The method can further comprise providing a secondary device comprising at least one processor and associated memory adapted to receive sensor data collected by the data collection device, and instructions which, when executed by the at least one processor, cause the at least one processor to interpret the sensor data obtained from the subject into descriptive factors indicative of a health condition of the subject; and output the descriptive factors.

The descriptive factors indicative of a health condition of the subject can comprise hydration, breathing patterns, body temperature, body and head position, body and head movement, clenching of the jaws, sleep phase, and nighttime mouth position. The secondary device can further comprise instructions which, when executed by the at least one processor, cause the at least one processor to provide the personalized treatment protocol, stage the health condition, measure the response to therapy, phenotype for selection to participate in drug trials, measure stability of an anatomical structure, or predict the rate of change of a health condition in the subject.

DETAILED DESCRIPTION

Figure 1:
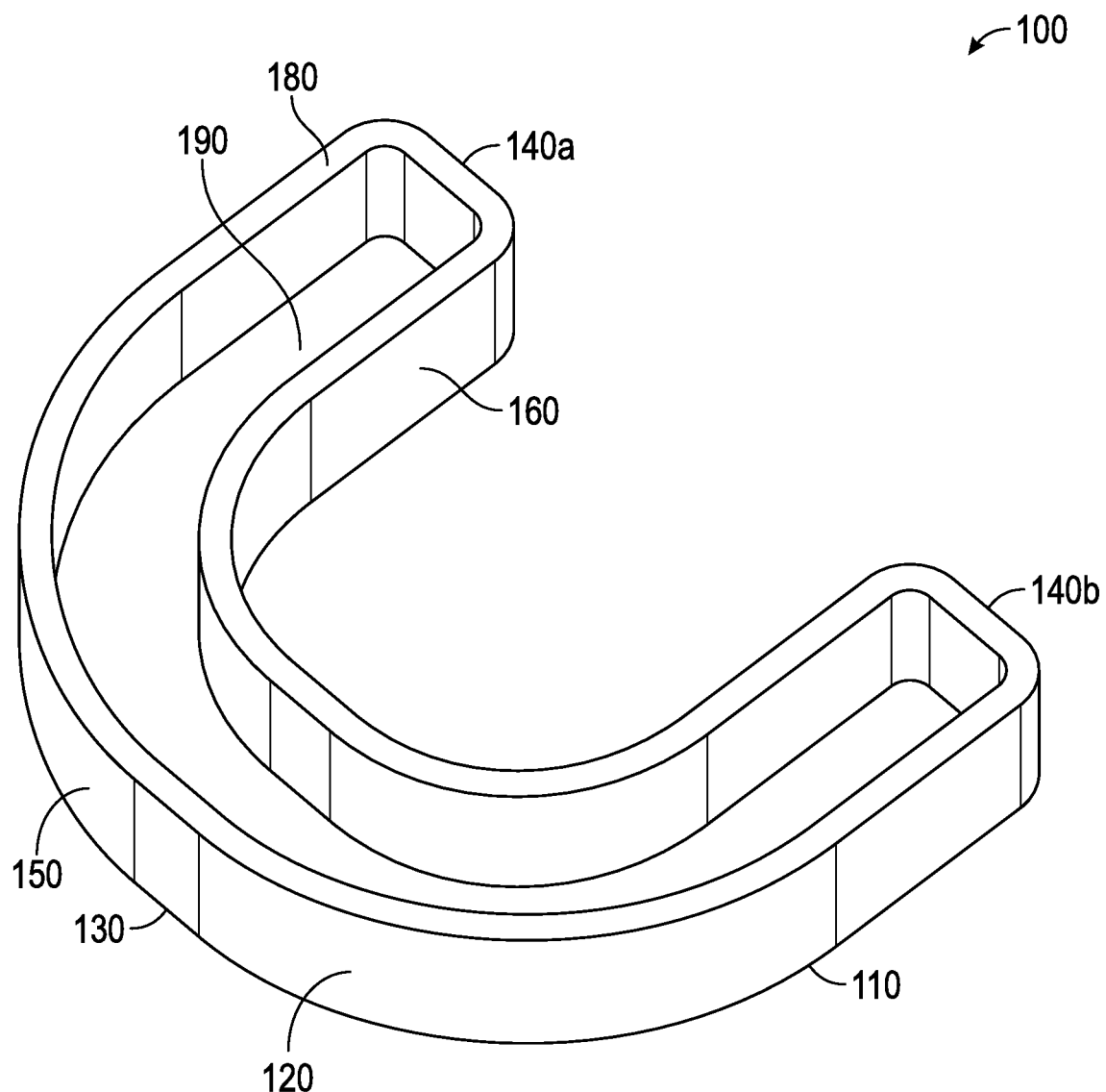
FIG. 1 is a top right perspective view of the device.

The devices, systems, methods, and computer program products for oral data collection will be understood from the accompanying drawings, taken in conjunction with the accompanying description. It is noted that, for purposes of illustrative clarity, certain elements in various drawings may not be drawn to scale. Several variations of the system are presented herein. It should be understood that various components, parts, and features of the different variations may be combined together and/or interchanged with one another, all of which are within the scope of the present application, even though not all variations and particular variations are shown in the drawings. It should also be understood that the mixing and matching of features, elements, and/or functions between various variations is expressly contemplated herein so that one of ordinary skill in the art would appreciate from this disclosure that the features, elements, and/or functions of one variation may be incorporated into another variation as appropriate, unless described otherwise.

Provided herein are systems, devices, methods, and computer program products for collecting oral data in the oral cavity of a subject for use in the healthcare field. The device can be worn by the user to continuously collect oral data normally not accessible to the user(s) or a designated official or healthcare professional. For instance, the device can be worn by a subject to collect oral data during exercise and during sleep.

The device is targeted for use in a method for determining a personalized treatment protocol, staging a given health condition, measuring response to therapy, phenotyping for selection to participate in drug trials, measuring stability of an anatomical structure, or predicting rate of change of a health condition in a subject in need thereof. The health conditions can be oral conditions as well as other health conditions that exhibit in data collected in the oral cavity. Additionally, medical oral data collected by the device can be used as part of a greater analytics medical network that incorporates machine learning, predictive analytics, information sharing, medical communications with professionals, and a virtual community where big data/trends are shared.

I. Device

One aspect of the present disclosure encompasses an oral data collection device. The device comprises a mouthguard with two or more sensors, a controller, a means for communicating sensor data, and a power source. The one or more sensors, controller, and power source are enclosed in the body of the device.

The mouthguard comprises an arch-shaped body comprising an external surface, an internal surface, a first biting surface, and a tray operable to engage a user's upper or lower teeth, the tray comprising a second biting surface opposite the first biting surface. It will be recognized that the arch-shaped body and the tray are of a size and shape appropriate for engaging with, and securing the mouthguard to the teeth of a wearer.

Materials suitable for manufacturing the mouthguard will be apparent to an individual of skill in the art. For instance, materials for the mouthguard may include, but are not limited to, one or more of the following materials: plastic, rubber, gel, metal, ceramic, and glass. Further, the mouthguard can be manufactured using more than one material. For example, the tray of the mouthguard can be manufactured of material suitable for securing the mouthguard to the teeth, whereas the body of the mouthguard can be manufactured using a material suitable for the function and protection of elements enclosed within the body of the mouthguard. The material could also be chosen to provide comfort for the wearer. Methods of manufacturing the mouthguard can and will vary depending on the material used for the product and the configuration of the product among other variables. For instance, the mouthguard can be manufactured using blow molding methods.

The device comprises one or more pressure sensors in the body of the mouthguard. Each sensor is operable to sense biting force exerted by the upper and lower teeth of the subject at the first and second biting surfaces. Pressure sensors are instruments or devices that translate the magnitude of the physical pressure exerted on the sensor into an output signal that can be used to establish a quantitative value for the pressure. There are many different types of pressure sensors known in the art, which function similarly but rely on different underlying technologies to make the translation between pressure and an output signal. Non-limiting examples of pressure sensor technologies include:

Potentiometric pressure sensors. Potentiometric pressure sensors use a Bourdon tube, capsule, or bellows which drives a wiper arm, providing relatively course pressure measurements.

Inductive pressure sensors. Inductive pressure sensors use a linear variable differential transformer (LVDT) to vary the degree of inductive coupling that occurs between the primary and secondary coils of the transformer.

Capacitive pressure sensors. Capacitive pressure sensors use a diaphragm that is deflected by the applied pressure, which results in a change in the capacitance value, which can then be calibrated to provide a pressure reading.

Piezoelectric pressure sensors. Piezoelectric pressure sensors rely on the ability of materials such as ceramic or metalized quartz to generate an electrical potential when the material is subjected to mechanical stress.

Strain gauge pressure sensors. Strain gauge pressure sensors rely on a measurement of the change in resistance that occurs in a material such as silicon when it is subjected to mechanical stress, known as the piezoresistive effect.

Variable reluctance pressure sensors. Variable reluctance pressure sensors make use of a diaphragm that is contained in a magnetic circuit. When pressure is applied to the sensor, the diaphragm deflection causes a change in the reluctance of the circuit and that change can be measured and used as an indicator of the applied pressure.

A pressure sensor suitable for a device of the instant invention can be any pressure sensor having an appropriate size and shape suitable for functionally enclosing the sensor in the body of the mouthguard, and capable of withstanding and measuring the entire range of a human's biting force, including the biting forces generated during bruxism. Biting during bruxism produces a pressure of about 100 lbs to 200 lbs (or about 2000 kPa). Accordingly, a pressure sensor of the disclosure can measure and withstand at least a pressure ranging from about 1 to about 5000 kPa, from about 100 to about 4000 kPa, or from about 100 to about 2000 kPa.

A pressure sensor can be a membrane pressure sensor or a force plate pressure sensor among others. In some aspects, the pressure sensor is a force plate sensor. Force plate sensors use one of several different types of sensors (load cells) to measure forces. Beyond vertical force, some force plate sensors can measure shear forces—i.e. lateral and horizontal forces. In some aspects, the pressure sensor is a force plate sensor. In some aspects, the pressure sensor is capable of measuring shear forces. In some aspects, the pressure sensor is a force plate pressure sensor capable of measuring shear forces. Commercially available force plate pressure sensors suitable for use in a device of the invention include MD30-60 Resistance-Type Thin Film Pressure Sensor, and the FC2311-0000-2000-L Force Sensors & Load Cells high compression load cell.

Pressure sensors suitable for the instant disclosure are operable to extrapolate velocity of movement (m/s), power (Watts), displacement (Meters), temporal parameters (seconds), and left/right asymmetry for bilateral systems. In conjunction with other measurements of the oral cavity of a subject such as 3D imaging of the oral cavity, force plate pressure sensors can calculate and predict tooth location and movement, in addition to measuring the biting force. Such measurements can enable a frame-by-frame video/playback view of tooth location and movement that, when mapped out over time, could predict the future state of oral health and placement, thereby allowing preventive measures to prevent such movement or the damage resulting from these movements.

In some aspects, the device comprises one or more pressure sensors at the first distal end of the body, one or more pressure sensors at the second distal end of the body, or one or more pressure sensors at the first distal end of the body and one or more pressure sensors at the second distal end of the body. Each sensor is operable to sense biting force exerted by the upper and lower molars of the subject at the first and second biting surface. In some aspects, the device comprises a pressure sensor at the first or second distal end of the mouthguard. In other aspects, the device comprises a first pressure sensor at the first distal end of the mouthguard and a second pressure sensor at the second distal end of the mouthguard.

In some aspects, the pressure sensor is a pressure sensor stack. Accordingly, the device comprises one or more pressure sensor stacks. The pressure sensor stack comprises at least two sensors arranged in a stack. In some aspects, the pressure sensor stack comprises a first pressure sensor and a second pressure sensor, wherein the first sensor is operable to sense the biting pressure of a bottom molar, and the second sensor is operable to sense the biting pressure of a top molar. In some aspects, the device comprises one or more pressure sensor stacks at the first distal end of the body, one or more pressure sensor stacks at the second distal end of the body, or one or more pressure sensor stacks at the first distal end of the body and one or more pressure sensor stacks at the second distal end of the body. Each sensor is operable to sense biting force exerted by the upper and lower molars of the subject at the first and second biting surface. In some aspects, the device comprises a pressure sensor stack at the first or second distal end of the mouthguard. In other aspects, the device comprises a first pressure sensor stack at the first distal end of the mouthguard and a second pressure sensor stack at the second distal end of the mouthguard.

The device also comprises a humidity sensor enclosed in the body of the mouthguard. The humidity sensor is operable to detect relative humidity in the breath of a user wearing the device. A humidity sensor suitable for a device of the instant invention can be any humidity sensor having an appropriate size and shape suitable for functionally enclosing the sensor in the body of the mouthguard. Further, a humidity sensor suitable for use in a device of the invention is generally waterproof to be capable of measuring relative humidity in the breath of a user, in the presence of saliva. Non-limiting examples of humidity sensors suitable for a device of the invention include the HIH-4000-004 humidity sensor from Honeywell, and HDC 1080 sensors from Texas Instruments.

The humidity sensor is enclosed in the body of the mouthguard such that a sensing surface of the sensor is in physical contact with the breath of the wearer. Further, the humidity sensor is in a location in the body of the device such that a sensing surface of the sensor is in optimal contact with exhaled or inhaled breath. For instance, a sensing surface can be in a cavity in the body of the mouthguard adjacent to, and in functional communication with an aperture extending from the external surface to the internal surface at the proximal end of the body of the mouthguard, wherein at least the sensing surface of the sensor is in contact with the breath of the user. Alternatively, the sensing surface is at the surface of the mouthguard at a location in the mouthguard capable of providing optimal contact with exhaled breath. For instance, the sensing surface can be at the internal surface of the mouthguard. In some aspects, a sensing surface of the humidity sensor is located off center at the internal surface of the proximal end of the mouthguard. In one aspect, the sensing surface of the sensor is located at left of center at the internal surface of the proximal end of the mouthguard. In another aspect, the sensing surface of the sensor is located right of center at the internal surface of the proximal end of the mouthguard.

A suitable humidity sensor can sense relative humidity in a range encompassing the relative humidity of the breath, including the low relative humidity of a user with xerostomia or halitosis. Xerostomia or dry mouth is a common, but sometimes overlooked, condition that is typically associated with salivary gland hypofunction (i.e., the objective measurement of reduced salivary flow). Reduced salivary flow can cause difficulties in tasting, chewing, swallowing, and speaking; it can also increase the chance of developing dental decay, demineralization of teeth, tooth sensitivity, and/or oral infections. There are a variety of potential causes of xerostomia, including adverse effects of medication, toxicity of chemotherapy and/or radiation therapy of the head and neck, autoimmune disease, other chronic disease, and nerve damage. Halitosis—or chronic bad breath—is something that mints, mouthwash or a good brushing cannot solve. Unlike "morning breath" or a strong smell that lingers after a tuna sandwich, halitosis remains for an extended amount of time and may be a sign of something more serious. Halitosis can be an indication of health conditions in the subject, including cavities and gum disease, mouth, nose and throat infections, dry mouth including xerostomia, smoking, tobacco, or other chronic conditions such as gastric reflux, diabetes, and liver or kidney disease.

Within the oral region of the human body there are many other opportunities for invaluable human information and health indicators to be more holistically understood. Accordingly, the device can further comprise sensors for use in collecting oral data in addition to biting pressure and relative humidity in the breath. Non-limiting examples of sensors include a temperature sensor, a microphone or vibration sensor, an oxygen sensor, a nine-axis inertial sensor, a pH or other biochemical sensor, or combinations thereof. Such sensors are known in the art, and suitable sensors can be identified experimentally. Other sensors capable of sensing oral biometric data are apparent to an individual of skill in the art.

In some aspects, the device comprises a temperature sensor. Body temperature has been measured orally for centuries, but has not been measured during sleep to measure parameters collected in conjunction with sleep phases, body position, hydration, and time, which in itself can reveal one's quality of sleep and habits at night. A temperature sensor can be, e.g., a diode type sensor, an external low-power temperature sensor such as the Texas Instruments LM94022 multi-gain sensor, or other appropriate type of temperature sensor. The temperature sensor can be operable to record oral temperatures, thereby providing potential heat-related oral and general health of a user. In some aspects, the temperature sensor can be an integrated humidity and temperature sensor. Such integrated sensor can include, e.g., the HDC 1080 sensors from Texas Instruments.

In some aspects, the device comprises a microphone or vibration sensor. A microphone or vibration sensor can be useful in detecting breathing patterns during sleep. The human breath soundwaves can provide information related to breathing conditions such as sleep apnea and snoring. The microphone/vibration sensor can be a unit similar to that of a 801S Vibration Sensor Module vibration Analog Output Sensitivity LM393 within the mainstream market. In some aspects, the microphone or vibration sensor is enclosed in an acoustic chamber in the body of the device. In some aspects, the microphone/vibration sensor is at the proximal end in the body of the mouthguard in an acoustic chamber that collects the soundwave of the human breath. In some aspects, the microphone/vibration sensor is in a protective compartment as described further below, wherein the protective compartment collects the soundwave of the human breath.

In some aspects, the device comprises a nine-axis inertial sensor enclosed in the body of the mouthguard. The inertial sensor comprises a three-axis magnetometer, a three-axis accelerometer, and a three-axis gyroscope, the three-axis magnetometer operable to provide a reference plane in relation to the earth's magnetic field for the three-axis accelerometer and the three-axis gyroscope. The nine-axis inertial sensor is adapted to sense the position and movement of the head and body of a subject wearing the device. Within the field, accelerometers have been used to detect impact during athletic activities, most notably within a football helmet that is connected to a mouthguard. In some aspects, the inertial sensor is located in the body of the mouthguard, at the proximal end of the mouthguard. Use of an inertial sensor in a device of the instant disclosure can detect the sudden/gradual movement of the head, the body, or both. For instance, the inertial sensor can track if an individual is upright, sleeping sideways, on back, or on belly which plays a large role with numerous medical and psychological indicators and patterns such as nightmares, stress, PTSD, or sleep apnea.

The device comprises a controller in the body of the mouthguard. The controller is in functional communication with the two or more sensors, and is operable to receive and communicate sensor data. In addition to receiving sensor data, the controller can include additional input components that permit input by a user (e.g., a touch screen display, a keyboard, a keypad, a mouse, a button, a switch, a microphone, etc.). The controller can also include output components that provide output information (e.g., a display, a speaker, one or more light-emitting diodes (LEDs), etc.).

The device further comprises a means for communication enclosed in the body of the device. The means for communication is operable to receive the sensor data from the controller and communicate the sensor data to a secondary device. The means for communication may include a transceiver-like component (e.g., a transceiver, a separate receiver and transmission source, etc.) that communicates the sensor data received by the controller to a secondary device, such as via a wireless connection using a wireless communication protocol, a wired connection, or a combination of wired and wireless connections. A wired connection can include an Ethernet interface, an optical interface, a coaxial interface, an infrared interface, a universal serial bus (USB) interface, and/or the like. A wireless communication protocol can include an NFC communication, a Radio-frequency identification (RFID) communication, Bluetooth, LTE, ZigBee, LoraWAN, Wi-Fi, and/or the like. In some aspects, the means of communication comprises a transmitter operable to communicate the oral data to the secondary device wirelessly using a wireless communication protocol. In some aspects, the means of communication comprises a transmitter operable to communicate the oral data to the secondary device wirelessly using Bluetooth.

The secondary device can be a stationary computing device such as a desktop computer. Alternatively, the secondary device can be a mobile computing device such as a cellular phone (e.g., a smartphone or standard cellular phone), a portable computer (e.g., a tablet computer, a laptop computer, etc.), a wearable device (e.g., a watch, a pair of glasses, a lens, clothing, and/or the like), a personal digital assistant (PDA), a computing device with no user interface, a cloud computing platform, and/or other like devices.

The device further comprises a power source functionally coupled to the controller and the two or more sensors. The power source can be a wired connection to an external power source. For instance, the power source can be rechargeable through a port defined in the device. The power source can also be a power storage device such as a conventional battery, capacitor, or electromagnetic power source. The power source can be removable, replaceable, rechargeable, and combinations thereof. For instance, if the power source is rechargeable, the power source can be rechargeable wirelessly or through a wired connection to an external power source. The power source can also be rechargeable by an electric generator that is powered by mechanical energy received from the subject. In this aspect, the electric generator can be configured to convert mechanical energy applied to the mouth guard by the subject (through, for example, biting down) into electrical energy.

In addition to the controller, the device can further comprise at least one processor and associated memory adapted to receive sensor data from the controller. In some aspects, the processor can be operable to assign one or more event times, wherein each event time indicates the time of a change in the state of a signal received from a sensor. In this aspect, the associated memory can be operable to receive and store the signals and/or outputs of the sensors of the device, and the one or more event times. The storage component may store information and/or software related to the operation and use of the controller. The storage component can include a random-access memory (RAM), a read only memory (ROM), and/or another type of dynamic or static storage device (e.g., a flash memory, a magnetic memory, an optical memory, etc.) that stores information and/or instructions for use by the controller.

In some aspects, it is contemplated that the processor can comprise means for generating an alarm in response to one or more inputs from a sensor. In these aspects, it is contemplated that the means for generating an alarm can comprise a conventional device for selectively generating optical, thermal, vibrational, and/or audible alarm signals.

Other components that may be included in the device can be a power button, controls for operating one or more components of the device, a component that provides output information from the controller (e.g., a display, a speaker, one or more light-emitting diodes (LEDs), etc.), or combinations thereof. For instance, when the means for communication is a Bluetooth module, the controls can be used to connect and pair the device to the secondary device. In some aspects, the power button can also be used as a means for controlling one or more of the components of the device.

It will be recognized that one or more of the components of the device, including the one or more sensors, the controller, the means for communication, the power source and any other electronic components, can be integrated onto a single circuit board for space saving. Further, one or more of the one or more sensors, the controller, the means for communication, the power source and any other electronic components can be enclosed in a protective compartment in the body of the mouthguard. For instance, the protective compartment can be water resistant, and can protect the components from biting forces and from the environment in the oral cavity, including saliva. The protective compartment can be sealed or can comprise a resealable opening for access to the components. In some aspects, one or more components of the device, including sensors, controllers, and communication means, are enclosed in a protective compartment in the mouthguard. In some aspects, when the protective compartment comprises a microphone/vibration sensor, the protective compartment is operable to provide an acoustic chamber that collects the soundwave of the human breath.

Figure 2:
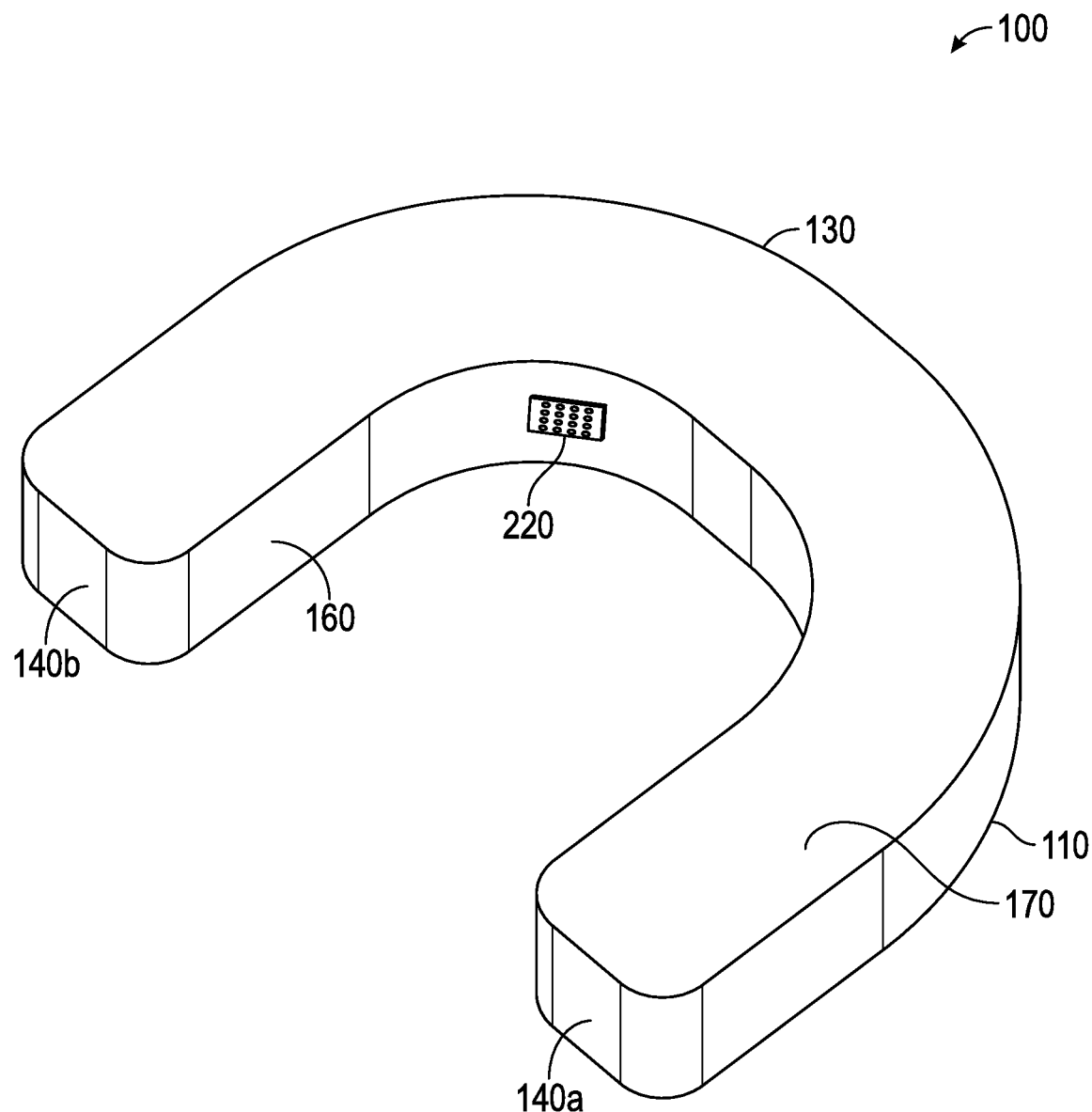
FIG. 2 is a bottom right perspective view of the device.
Figure 3:
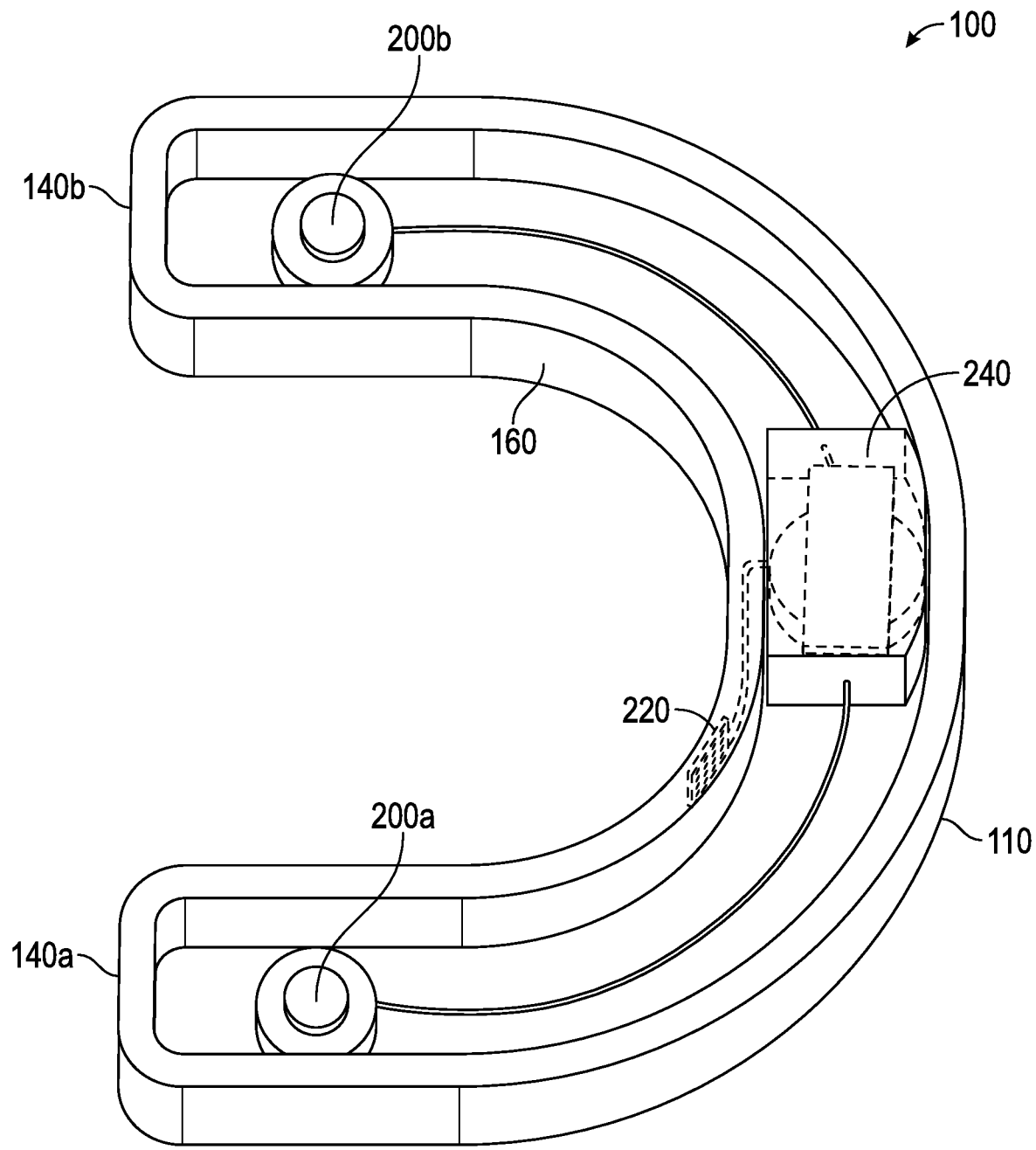
FIG. 3 is a top left perspective view of the side of the device with the top biting surface removed thus exposing the components enclosed in the device.
Figure 4:
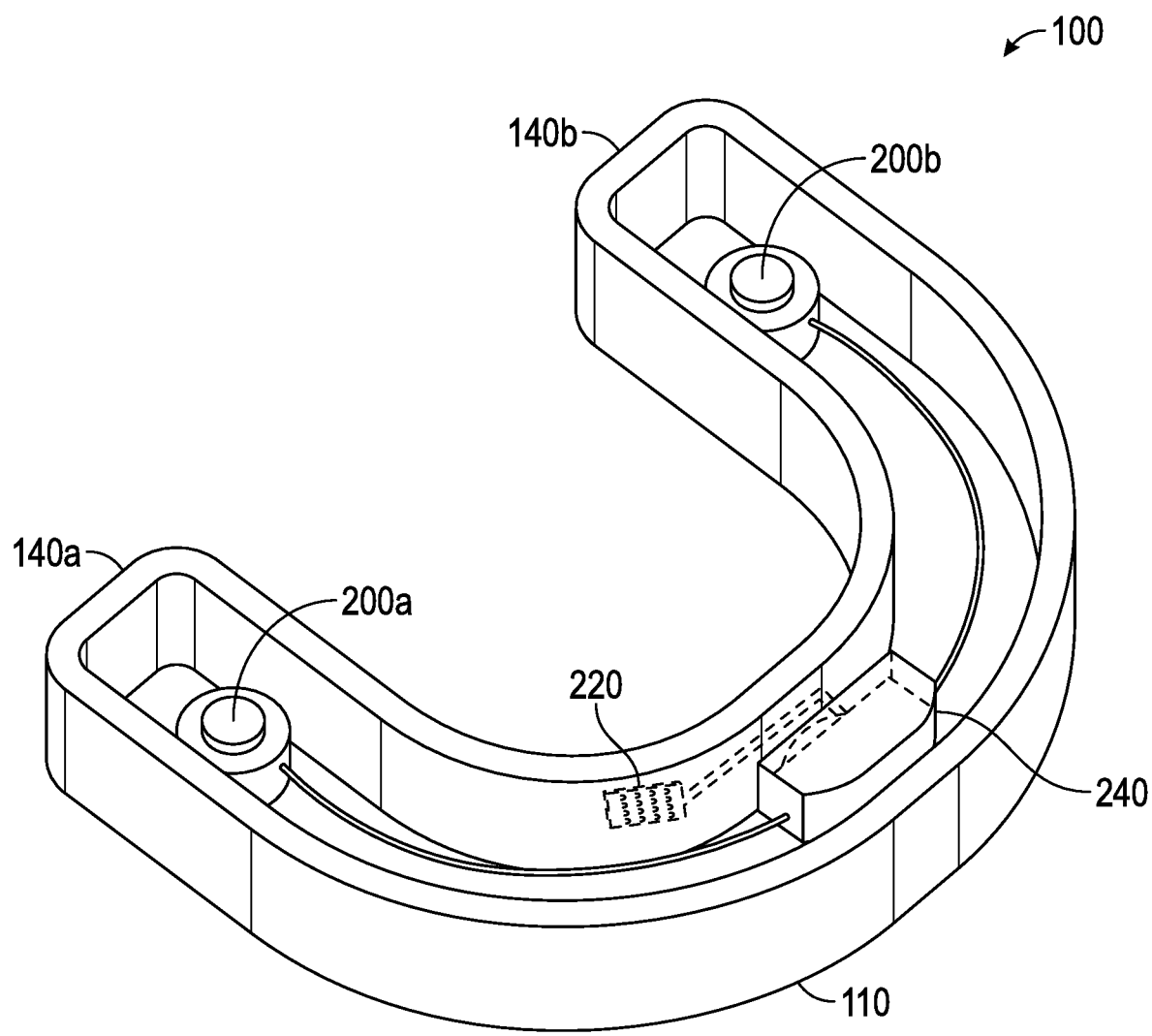
FIG. 4 is a top left perspective view of the front of the device with the top biting surface removed thus exposing the components enclosed in the device.
Figure 5:
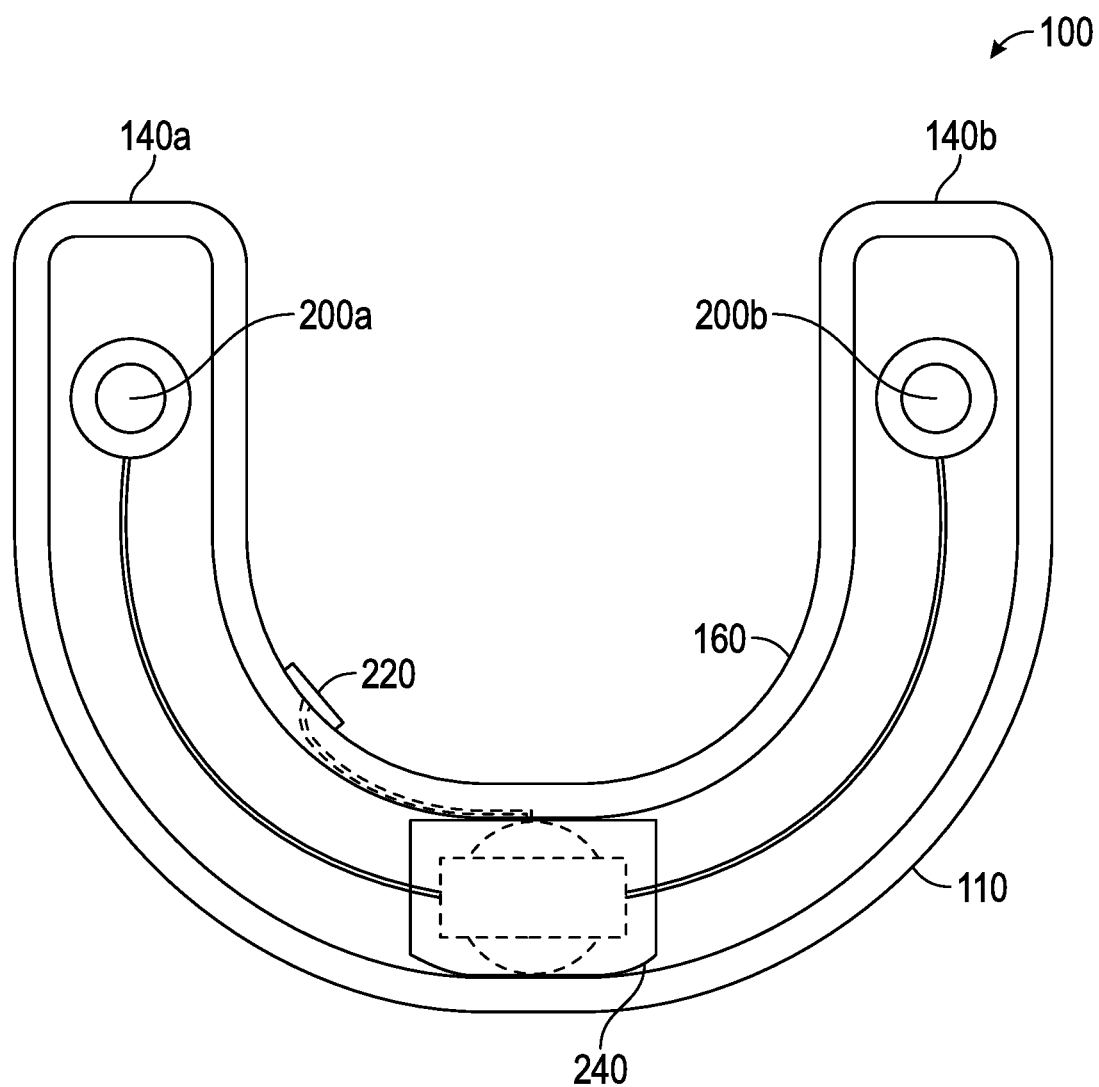
FIG. 5 is a top view of the device with the top biting surface removed thus exposing the components enclosed in the device.
Figure 6:
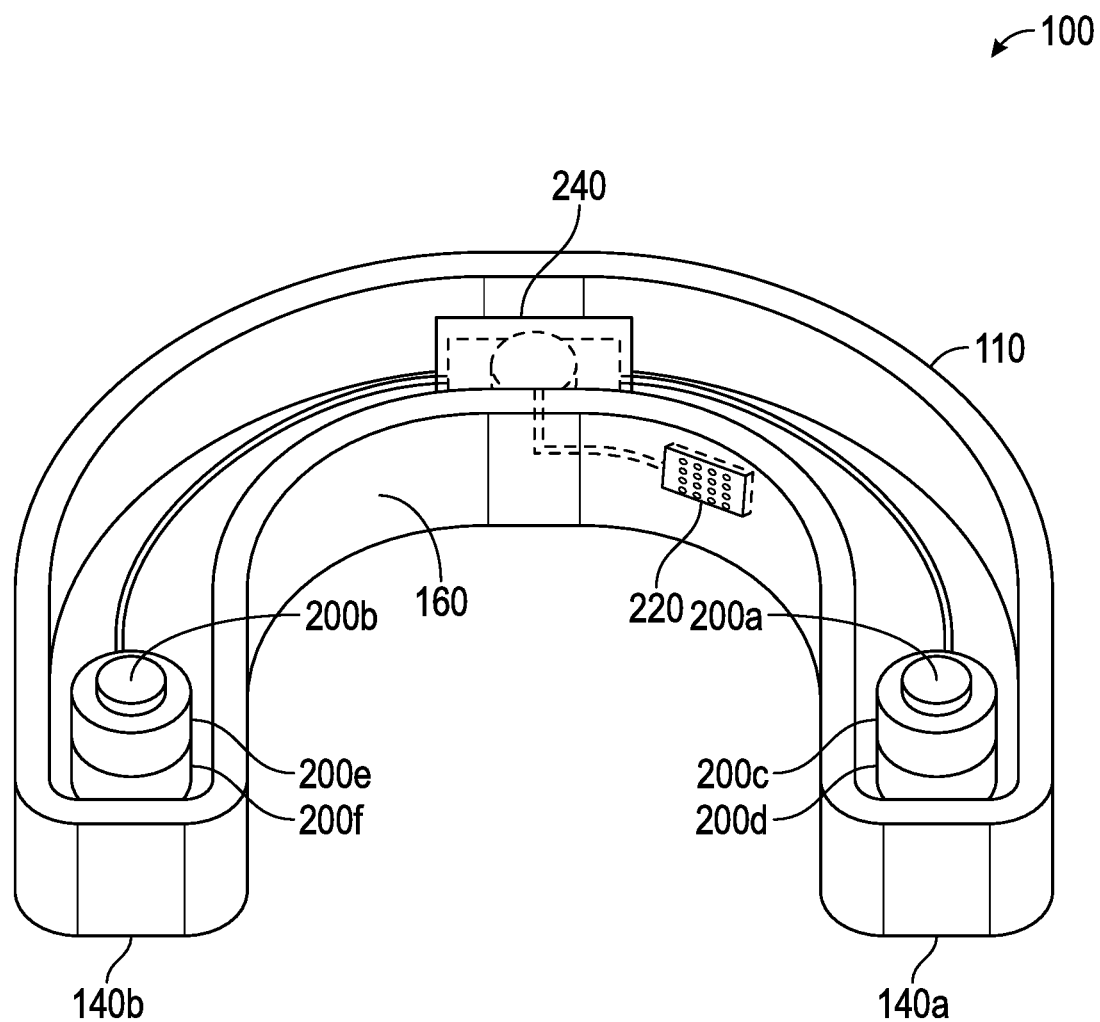
FIG. 6 is a top perspective view of the back of the device with the top biting surface removed thus exposing the components enclosed in the device.
Figure 7:
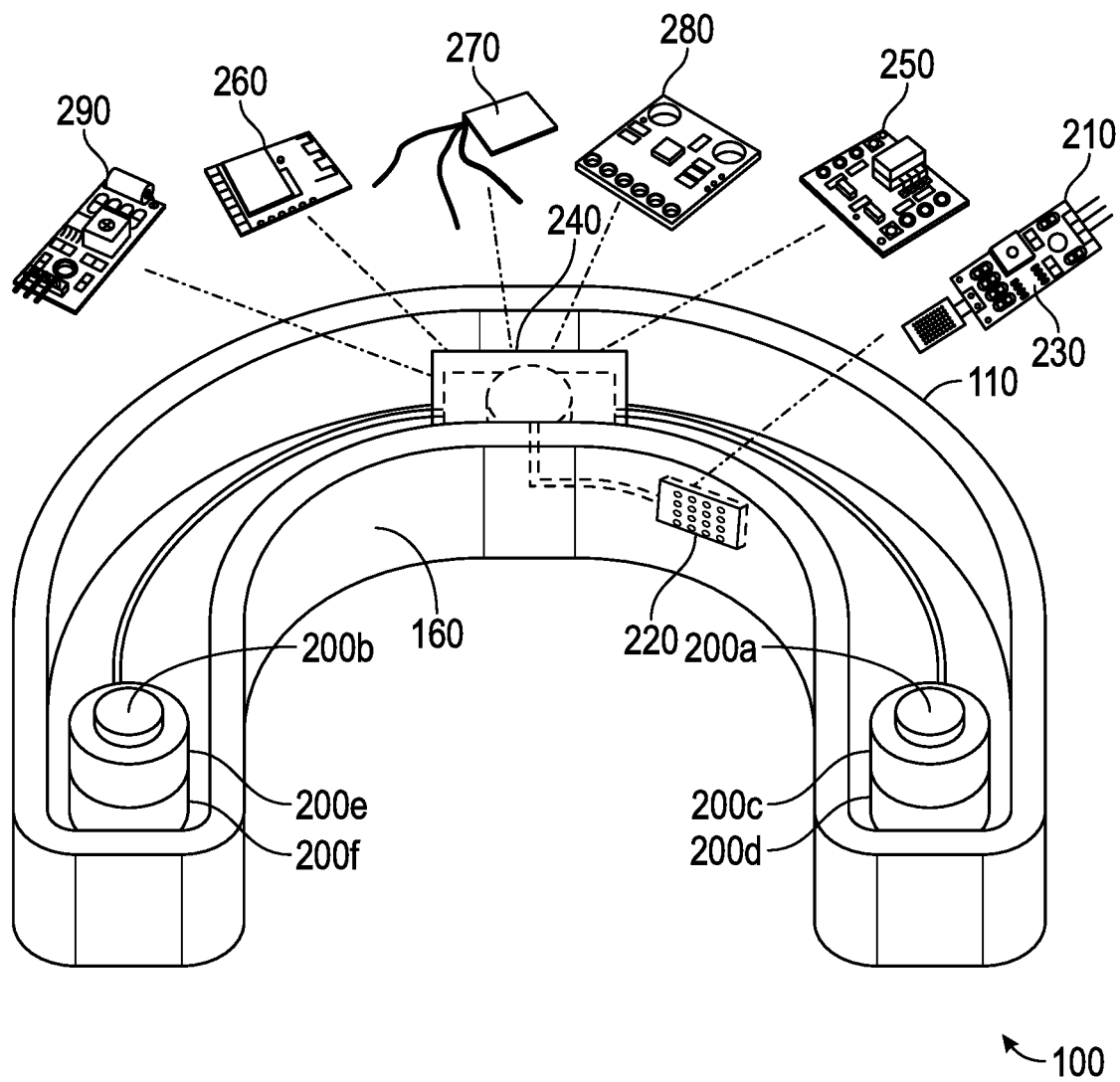
FIG. 7 is a perspective view of the back of the device with the top biting surface removed thus exposing the components enclosed in the device with an exploded view of the components of the device in the protective enclosure.

Referring to FIG. 1 and FIG. 2, shown is a graphical representation illustrating an aspect of the oral data collection device 100. The device 100 comprises a mouthguard 110, the mouthguard comprising an arch-shaped body 120, a proximal end 130, a first distal end 140*a*, and a second distal end 140*b*, an external surface 150, and an internal surface 160. The mouthguard 110 further comprises a first biting surface 170 (not shown in FIG. 2) and a tray 180 operable to enclose a user's upper or lower teeth, the tray comprising a second biting surface 190 (not shown in FIG. 1) opposite the first biting surface 170.

Referring now to FIGS. 3-7, the device 100 comprises a first pressure sensor 200a in the body 120 of the device 100 at the first distal end 140a and a second pressure sensor 200b at the second distal end 140b of the body 120. Each sensor is operable to sense biting force exerted by the upper and lower molars of the subject at the first biting surface 170 and second biting surface 190. In one alternative aspect of the device shown in FIGS. 6 and 7, the device comprises a first pressure sensor stack 200a comprising a first pressure sensor 200c and a second pressure sensor 200d, and a second pressure sensor stack 200b comprising a first pressure sensor 200e and a second pressure sensor 200f.

The device further comprises a humidity sensor 210 comprising a sensing surface 220. The sensing surface 220 is exposed at right of center of the internal surface 160 of the mouthguard 110. Electronic components 230 of the humidity sensor 210 are enclosed in the protective compartment 240 of the mouthguard 110.

The device 100 further comprises a controller 250 in the protective compartment 240 of the mouthguard 110, a Bluetooth module 260 for communicating the sensor data received by the controller 250, and a battery 270 to power the device. In this aspect, the device further comprises a nine-axis sensor 280 and a microphone/vibration sensor 290.

II. Methods

Another aspect of the present disclosure encompasses methods of collecting oral data in the oral cavity of a subject. In a method of the invention, the device is worn by the subject by positioning the device in engagement with at least one of the upper teeth or the lower teeth of the subject. In some aspects, the device is worn by the subject during sleep. In other aspects, the device is worn by the subject during exercise. In operation, it is contemplated that data points can be collected and then processed according to a predetermined algorithm, such as a series of equations and/or lookup tables. For instance, the data can be used to assign one or more event times, wherein each event time indicates the time of a change in the state of a signal received from a sensor. Further, data points collected and/or assigned event times can be translated into health score using a predetermined algorithm.

The collected oral data or the event times or health score derived from the data can be used in determining a personalized treatment protocol, staging a given health condition, measuring response to therapy, phenotyping for selection to participate in drug trials, measuring stability of an anatomical structure, or predicting rate of change of the given disease in a subject in need thereof. The subject has or is suspected of having one or more health conditions in the oral cavity or a health condition exhibited in the oral cavity. As used herein, the term "exhibited in the oral cavity" refers to symptoms of health conditions in the subject other than health conditions in the oral cavity, but can be detected using biometric data collected in the oral cavity. Non-limiting examples of health conditions include concussions and head injuries, bruxism, xerostomia, sleep apnea, nightmares, PTSD, anxiety, insomnia, tooth infection, tooth decay, tooth damage, and psychological disorders such as psychosis, sleep walking, and combinations thereof among other disorders. In some aspects, the health condition is bruxism. In other aspects, the health condition is xerostomia.

The method further comprises using the oral cavity data collected from the subject to develop a database of biometric measurements obtained from the subject alone or in combination with data measurements obtained from other subjects, for providing information to the subject or healthcare provider regarding historical physiological characteristics of the subject, thereby providing a means for determining health conditions and unusual behaviors. The collected data can be used in combination with descriptive information comprising one or more data elements relating to the subject. The data elements can include the results of clinical tests normally performed during a regular visit by the subject to a physician, including weight, height, blood pressure, pulse, and results of blood tests such as cholesterol levels, comprehensive metabolic panel, and lipid panel, among others. The data elements can also include information and results of clinical tests obtained during diagnosis of a health condition. For instance, when the health condition is bruxism, non-limiting examples of data elements can include tooth wear, headaches, anxiety, jaw pain, abnormal sleeping patterns, changes in sleep positioning, changes in bite force distribution, changes in movement while sleeping, sleep loss, behavioral changes (e.g., heightened stress, anxiety), and combinations thereof.

III. Computer-Implemented Methods and Systems

One aspect of the present disclosure encompasses a computer-implemented method for collecting biometric data in the oral cavity of a subject. The method comprises providing an oral data collection device of Section I, and a computer system having at least one processor and associated memory comprising instructions to process the oral data collected by the device. The computer system having at least one processor and associated memory can be a processor further comprised in the device. Alternatively, the computer system can be a secondary device. The device and data points and methods of processing the data points can be as described above in Sections I and II. The computer system comprises instructions to receive at least one data point from the device, and process the at least one data point according to a predetermined algorithm, such as a series of equations and/or lookup tables.

Another aspect of the present disclosure encompasses at least one non-transitory computer readable medium. The medium stores instructions which, when executed by at least one processor, cause the at least one processor to receive at least one data point from the device, and process the at least one data point according to a predetermined algorithm, such as a series of equations and/or lookup tables.

The medium can further comprise instructions, which when executed by the at least one processor, cause the at least one processor to display the processed at least one data point. Further, the medium can also comprise instructions, which when executed by the at least one processor, cause the at least one processor to generate a report of the processed at least one data point.

Yet another aspect of the present disclosure encompasses a system for collecting biometric data in the oral cavity of a subject. The system comprises an oral data collection device collecting biometric data in the oral cavity of the subject. The device and data points and methods of processing the data points can be as described above in Sections I and II. The system further comprises a processor. The processor comprises a memory having instructions stored thereon, wherein the instructions, when executed by the processor, cause the processor to perform the methods disclosed herein. In one aspect, the system also comprises an interface unit to display an output wherein the output is used for at least one of determining a personalized treatment protocol for the subject, staging the given disease in a patient, measuring response to therapy, phenotyping for patient selection to participate in drug trials, measuring stability of an anatomical structure, or predicting rate of change of the given disease. The interface unit may be, for example, a display device such as, but not limited to a CRT (cathode ray tube) or LCD (liquid crystal display) monitor. The display device can display information to the user and may include or be in operative communication with an input device such as a keyboard, touchscreen, and/or pointing device (e.g., a mouse or a trackball). An input device may alternatively, or in addition, be configured to receive and transmit a signal based on other types of user input, such as voice instruction, or body movement.

In some aspects, the processor is further configured by way of processor-executable instructions to obtain descriptive information relating to the subject, the descriptive information comprising one or more data elements. The descriptive information can be as described In Section II above.

It should be understood that the disclosed methods, method steps and/or processor-executable instructions can be implemented or executed by means of any digital electronic system, computer hardware, firmware, software, or any combinations thereof. A processor may take the form of a programmable processor, a computer, or multiple computers, which may be programmed to perform the disclosed methods using any programming language. A program of instructions may comprise a stand-alone program or may have two or more modules, components, subroutines, or the like as known in the art of computer programming. Method steps can be performed by one or more programmable processors executing a computer program to perform functions or aspects of the methods, by operating on input data and generating output information.

A processor may be configured, by way of processor-executable instructions, to receive instructions and data from a memory device, which can be configured for storing instructions and data. A processor, or a computer containing a processor, may be in operative communication with at least one or more mass storage devices for storing data (e.g., magnetic, magneto-optical disks, or optical disks), such that the processor can receive data from or transfer data to such storage device(s). For example, data and/or instruction communications can be performed over a digital communications network.

It should be further understood that the disclosed methods, method steps and/or processor-executable instructions can be performed by a distributed computing system. A distributed computing system includes, for example, a front-end (user-end) interface, middleware, and a back-end, or any combination of two or more of these elements. A front-end component can be, for example, a client computer configured by way of processor-executable instructions to display a graphical user interface through which a user can interact with and provide input to the system. An interface can be embodied in a Web browser interface. A middleware component can be, for example, an application server. A back-end component can be, for example, a data server. Any or all of the components of such a distributed system can be in operative communication by way of one or more digital communications networks, which may be wired and/or wireless networks.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As used herein, the terms "communication" and "communicate" may refer to the reception, receipt, transmission, transfer, provision, and/or the like, of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. Alternatively, a first unit may be in communication with a second unit if at least one intermediary unit (e.g., a third unit located between the first unit and the second unit) processes information received from the first unit and communicates the processed information to the second unit.

As used herein, the term "computing device" may refer to one or more electronic devices that are operable to directly or indirectly communicate with or over one or more networks. The computing device may be a mobile device. As used herein, the term "mobile device" may refer to one or more portable electronic devices operable to communicate with one or more networks. As an example, a mobile device may include a cellular phone (e.g., a smartphone or standard cellular phone), a portable computer (e.g., a laptop computer, etc.), a wearable device (e.g., a watch, pair of glasses, lens, clothing, and/or the like), a portable computer with no user interface, a personal digital assistant (PDA), and/or other like devices. The computing device may also be a desktop computer. Furthermore, the term "computer" may refer to any computing device that includes the necessary components to receive, process, and output data, and normally includes a display, a processor, a memory, an input device, and a network interface.

As used herein, the term "application" or "application program interface" (API) refers to computer code, a set of rules, or other data sorted on a computer-readable medium that may be executed by a processor to facilitate interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, etc.).

As various changes could be made in the above-described cells and methods without departing from the scope of the invention, it is intended that all matter contained in the above description shall be interpreted as illustrative and not in a limiting sense.

What is claimed is:
1. An oral data collection device, comprising:
   a. a mouthguard, the mouthguard comprising:
      i. an arch-shaped body comprising a proximal end, a first distal end, and a second distal end, an external surface, an internal surface, a first biting surface, and a tray operable to engage the upper or lower teeth of a subject, the tray comprising a second biting surface opposite the first biting surface;
   b. sensors in the body of the mouthguard, the sensors comprising:
      i. a first pressure sensor stack at the first distal end of the mouthguard and a second pressure sensor stack at the second distal end of the mouthguard, wherein each pressure sensor stack comprises a first pressure sensor and a second pressure sensor arranged in a stack;
      ii. a humidity sensor operable to sense relative humidity in the breath of a user wearing the device; and
      iii. a microphone or vibration sensor;
   c. a controller in the body of the mouthguard, wherein the controller is in functional communication with the sensors, and wherein the controller is operable to receive and communicate sensor data;
   d. a means for communication in the body of the mouthguard, wherein the means for communication is operable to receive the sensor data from the controller and communicate the sensor data to a secondary device; and
   e. a power source functionally coupled to the controller and the one or more sensors;
   wherein each pressure sensor is a force plate pressure sensor, and
   wherein the controller is configured to receive data from each pressure sensor, and extrapolate the received data to obtain velocity of movement (m/s), power (Watts), displacement (Meters), temporal parameters (seconds), and left/right asymmetry for bilateral systems.

2. The device of claim 1, wherein each pressure sensor is operable to measure shear forces.

3. The device of claim 1, wherein the first sensor of each pressure sensor stack is operable to sense the biting pressure of a bottom molar, and the second sensor of each pressure sensor stack is operable to sense the biting pressure of a top molar.

4. The device of claim 1, wherein a sensing surface of the humidity sensor is at the internal surface off center of the proximal end of the mouthguard.

5. The device of claim 1, further comprising an oxygen sensor, a nine-axis inertial sensor, a pH or other biochemical sensor, or combinations thereof.

6. The device of claim 5, wherein the nine-axis inertial sensor is enclosed in the body of the mouthguard, and comprises a three-axis magnetometer, a three-axis accelerometer, and a three-axis gyroscope, the three-axis magnetometer operable to provide a reference plane in relation to earth's magnetic field for the three-axis accelerometer and the three-axis gyroscope, wherein the nine-axis inertial sensor is adapted to sense a position and movement of the head and body of a user.

7. The device of claim 5, wherein the temperature sensor, humidity sensor, and oxygen sensor are an integrated temperature, humidity, and oxygen sensor.

8. The device of claim 5, wherein the microphone or vibration sensor is enclosed in an acoustic chamber in the body of the mouthguard.

9. The device of claim 1, wherein the means of communication comprises a transmitter operable to communicate sensor data to the secondary device wirelessly using a wireless communication protocol.

10. The device of claim 1, wherein the secondary device is a desktop computer, a mobile computing device, a wearable device, a personal digital assistant, a computing device with no user interface, a cloud computing platform, or a combination thereof.

11. The device of claim 1, wherein the device further comprises a protective compartment housing one or more of the sensors, the controller, the means for communication, and the power source.

12. A medical analytics system comprising:
   a. an oral data collection device of claim 1; and
   b. a secondary device comprising at least one processor and associated memory adapted to receive sensor data collected by the data collection device, and instructions which when executed by the at least one processor, cause the at least one processor to:
      i. interpret the sensor data obtained from a subject into descriptive factors indicative of a health condition of the subject; and
      ii. output the descriptive factors.

13. The system of claim 12, wherein the descriptive factors indicative of a health condition of the subject comprise hydration, breathing patterns, body temperature, body and head position, body and head movement, clenching of the jaws, sleep phase, and nighttime mouth position.

14. The system of claim 12, wherein the secondary device further comprises instructions which when executed by the at least one processor, cause the at least one processor to provide a personalized treatment protocol, stage a health condition, measure a response to therapy, phenotype for selection to participate in drug trials, measure stability of an anatomical structure, or predict a rate of change of a health condition in the subject.

15. A method of determining a personalized treatment protocol, staging a given health condition, measuring response to therapy, phenotyping for selection to participate in drug trials, measuring stability of an anatomical structure, or predicting rate of change of a health condition in a subject in need thereof, the method comprising:
   a. providing or having provided the device of claim 1 to the subject for wearing by the subject during sleep; and
   b. interpret the sensor data obtained from the subject into descriptive factors indicative of a health condition of the subject to determine the personalized treatment protocol, stage the given health condition, measure response to therapy, phenotype for selection to participate in drug trials, measure stability of an anatomical structure, or predict rate of change of a given health condition in the subject.

16. The method of claim 15, wherein the method further comprises providing a secondary device comprising at least one processor and associated memory adapted to receive sensor data collected by the data collection device, and instructions which when executed by the at least one processor, cause the at least one processor to:
   a. interpret the sensor data obtained from the subject into descriptive factors indicative of a health condition of the subject; and
   b. output the descriptive factors.

17. The method of claim 16, wherein the descriptive factors indicative of a health condition of the subject comprise hydration, breathing patterns, body temperature, body and head position, body and head movement, clenching of the jaws, sleep phase, and nighttime mouth position.

18. The method of claim 16, wherein the secondary device further comprises instructions which when executed by the at least one processor, cause the at least one processor to provide the personalized treatment protocol, stage the health condition, measure the response to therapy, phenotype for selection to participate in drug trials, measure stability of an anatomical structure, or predict the rate of change of a health condition in the subject.

* * * * *